(12) United States Patent
Jain et al.

(10) Patent No.: US 8,664,452 B2
(45) Date of Patent: Mar. 4, 2014

(54) PROCESS FOR PREPARING EXTRA PURE 2, 6-DIISOPROPYL PHENOL

(75) Inventors: Kirti Prakash Jain, Udaipur (IN); Dhananjay Uddhavrao Edaki, Aurangabad (IN); Harpreet Singh Minhas, Mumbai (IN); Gurpreet Singh Minhas, Mumbai (IN)

(73) Assignee: Harman Finochem Limited, Mumbai, IN (US)

( * ) Notice: Subject to any disclaimer, the term of this patent is extended or adjusted under 35 U.S.C. 154(b) by 0 days.

(21) Appl. No.: 13/578,456

(22) PCT Filed: Aug. 10, 2010

(86) PCT No.: PCT/IN2010/000527
§ 371 (c)(1),
(2), (4) Date: Aug. 10, 2012

(87) PCT Pub. No.: WO2011/161687
PCT Pub. Date: Dec. 29, 2011

(65) Prior Publication Data
US 2013/0072573 A1 Mar. 21, 2013

(30) Foreign Application Priority Data
Jun. 23, 2010 (IN) .......................... 1862/MUM/2010

(51) Int. Cl.
*C07C 39/00* (2006.01)

(52) U.S. Cl.
USPC ........................................................ 568/716

(58) Field of Classification Search
USPC ............................ 514/731; 568/716; 562/475
See application file for complete search history.

(56) References Cited

U.S. PATENT DOCUMENTS

| | | |
|---|---|---|
| 2,207,753 A | 7/1940 | Moyle |
| 2,831,898 A | 4/1958 | Ecke |
| 3,029,276 A | 4/1962 | Hausweiler |
| 3,271,314 A | 9/1966 | Ecke |
| 3,367,981 A | 2/1968 | Napolitano |
| 3,766,276 A | 10/1973 | Goddard |
| 4,275,248 A | 6/1981 | Firth |
| 4,391,998 A | 7/1983 | Wu |
| 4,474,368 A | 10/1984 | Peter, III et al. |
| 4,774,368 A * | 9/1988 | Brackenridge ............... 568/796 |
| 5,264,085 A | 11/1993 | Inaba et al. |
| 5,589,598 A | 12/1996 | Paiocchi |
| 5,591,311 A | 1/1997 | Ramachandran |
| 5,696,300 A | 12/1997 | Bellani et al. |
| 5,705,039 A | 1/1998 | Clarke et al. |
| 6,362,234 B1 | 3/2002 | Hendler |

FOREIGN PATENT DOCUMENTS

| | | |
|---|---|---|
| CN | 1197055 | 10/1998 |
| EP | 169359 | 1/1986 |
| EP | 0511947 | 11/1992 |
| GB | 1318100 | 5/1973 |
| SU | 443019 | 5/1975 |
| WO | 0034218 | 6/2000 |
| WO | 0187289 | 11/2001 |
| WO | 2005033279 | 4/2005 |

OTHER PUBLICATIONS

Ickx et al. CAS: 130: 232379, 1999.*
Baltaksne et al. CAS: 82: 16554, 1975.*
International Search Report for PCT/IN2010/000527dated Mar. 31, 2011.

* cited by examiner

Primary Examiner — Rei-tsang Shiao
(74) Attorney, Agent, or Firm — Kramer Amado, P.C.

(57) ABSTRACT

Disclosed herein is a process for the preparation of highly pure 2,6-diisopropyl phenol (Formula I), which comprises reacting p-hydroxy benzoic acid (Formula II) with an alkylating agent in presence of aq. mineral acid followed by basification and subsequent washings to yield 4-hydroxy-3,5-diisopropylbenzoic acid (Formula III) free of dimer impurity, 4,4'-oxydibenzoic acid of Formula IV, ether impurity 3,5-di(propan-2-yl)-4-(propan-2-yloxy)benzoic acid of Formula V and the monoalkylated impurity 4-hydroxy-3-(propan-2-yl)benzoic acid of Formula VI; and decarboxylating 4-hydroxy-3,5-diisopropylbenzoic acid (Formula III) in presence of high boiling solvent and sodium hydroxide as a catalyst at high temperature to yield 2,6-diisopropyl phenol substantially free of ether impurity 1,3-di(propan-2-yl)-2-(propan-2-yloxy)benzene of Formula VII and monoalkylated phenol impurity 2-(propan-2-yl) phenol of Formula VIII. Propofol prepared by the process of the present invention is suitable for pharmaceutical use.

16 Claims, No Drawings

PROCESS FOR PREPARING EXTRA PURE 2, 6-DIISOPROPYL PHENOL

FIELD OF INVENTION

The present invention relates to a process for preparation of highly pure 2,6-diisopropyl phenol suitable for pharmaceutical use.

BACKGROUND OF INVENTION 2,6-diisopropylphenol, commonly known as "Propofol", is a short-acting, intravenously administered hypnotic agent. It is used as a general anesthetic or as a soporifacient for mechanically ventilated adults, and for procedural sedation.

2,6-diisopropylphenol has several mechanisms of action, both through potentiation of $GABA_A$ receptor activity, thereby slowing the channel-closing time and also acting as a sodium channel blocker. Recent research has also suggested that the endocannabinoid system may contribute significantly to anesthetic action of 2,6-diisopropylphenol and to its unique properties. 2,6-diisopropylphenol is highly protein-bound in vivo and is metabolized by conjugation in the liver. Its rate of clearance exceeds hepatic blood flow, suggesting an extrahepatic site of elimination as well.

Generally, 2,6-diisopropyl phenol is administered intravenously; hence the purity requirement is very high. For most purposes, ideal purity for 2,6-diisopropylphenol has to be more then 99.9%. The commercially available 2,6-diisopropylphenol is about 97% pure. The said product typically contains unreacted phenol, one or more monoalkylphenols, one or more dialkylphenol isomers other than the desired 2,6-dialkylphenol isomer.

A myriad of patents/patent applications have been filed across globe for preparation and purification of 2,6-diisopropylphenol, namely U.S. Pat. No. 5,696,300, U.S. Pat. No. 4,275,248, U.S. Pat. No. 3,029,276, WO2005033279, CN1197055, WO200034218, EP169359, U.S. Pat. No. 3,367,981, U.S. Pat. No. 3,271,314, U.S. Pat. No. 3,766,276, SU170505, U.S. Pat. No. 2,831,898, U.S. Pat. No. 2,207,753, GB1318100, U.S. Pat. No. 4,391,998, U.S. Pat. No. 4,774,368, U.S. Pat. No. 5,589,598 and U.S. Pat. No. 6,362,234.

EP0511947 discloses purification of 2,6-diisopropylphenol (Propofol). Accordingly, Propofol obtained by alkylation of propene with phenol is purified by crystallization as such at a temperature from −20° C. to −10° C. In an alternate method, said patent discloses purification of Propofol by crystallization from non-polar solvents, such as, petrol ether or hexane. The solvent residues are then removed either by distillation or evaporation and the product itself is recovered as a single fraction in the distillation. However, such a procedure is not well suited for use in a large scale commercial operation.

U.S. Pat. No. 5,264,085 describe a method of continuously separating components of a hydrous phenol mixture containing methanol by distillation. The method involves recovering methanol from the top of a single distillation column, dragging water containing phenols as a side stream from the recovery section of the distillation column and the dehydrated phenols as a bottom product.

U.S. Pat. No. 5,705,039 discloses a process for the purification of impure 2,6-diisopropylphenol which comprises: a) subjecting the impure 2,6-diisopropylphenol to a first continuous distillation in a single distillation column in an inert environment to produce (i) a first overhead distillate of impurities boiling below the boiling point of 2,6-diisopropylphenol at the prevailing pressure and (ii) first column bottoms enriched in 2,6-diisopropylphenol; b) collecting, cooling and storing the first column bottoms while continuously maintaining them in an inert environment; c) discontinuing the first continuous distillation; and d) subjecting said first column bottoms to a second continuous distillation in an inert environment in the same single distillation column to produce a second overhead distillate composed of purified 2,6-diisopropylphenol the process is however tedious and not economically viable.

U.S. Pat. No. 5,591,311 describes the process of purification of 2,6-diisopropylphenol which involves washing the mixture with aqueous alkali metal hydroxide solution in an inert atmosphere and separating the aqueous and organic phases, washing the resulting organic phase with water, and then subjecting the water-washed organic phase to distillation in an inert environment to recover purified diisopropylphenol (DIP).

U.S. Pat. No. 5,589,598 describes a process for the purification of 2,6-diisopropylphenol (Propofol) by transformation of the crude propofol into its ester with a carboxylic or sulphonic acid, followed by crystallization and hydrolysis.

Propofol is generally prepared from phenol and propene by Friedel-Crafts-alkylation, whereby in the reaction, besides the desired product, small amounts of other isomers and phenol derivatives are formed thus affecting the purity of the product. The major contaminants being 2,4- and 2,5-diisopropyl phenol, 2,4,6-triisopropyl phenol, and 1-isopropoxy-2,4-diisopropylbenzene having small differences in their boiling points.

In view of the above drawbacks in the preparation of Propofol there remains a need to develop a process for the preparation of 2,6-diisopropylphenol (Propofol) with high purity suitable for pharmaceutical use and which is simple, economical for large scale manufacturing.

SUMMARY OF INVENTION

Accordingly, the present invention discloses economical process for preparation of highly pure 2,6-diisopropylphenol.

In an aspect of the reaction, p-hydroxy benzoic acid is reacted with an alkylating agent in presence of acidic and/or dehydrating medium at 60-65° C. followed by basification to obtain 4-hydroxy-3,5-diisopropyl benzoic acid of Formula III.

Besides the desired product, significant amounts of contaminants are also formed such as ether impurity 3,5-di(propan-2-yl)-4-(propan-2-yloxy)benzoic acid of Formula V, dimer impurity, 4,4'-oxydibenzoic acid of Formula IV, and the monoalkylated impurity 4-hydroxy-3-(propan-2-yl)benzoic acid of Formula VI which are removed by simple washings with solvent mixtures.

Purification of 4-hydroxy-3,5-diisopropyl benzoic acid prior to decarboxylation stage inhibit impurities development at Propofol formation.

In another aspect, 4-hydroxy-3,5-diisopropyl benzoic acid of Formula III substantially free from impurities of Formula IV, V and VI, is then subjected to decarboxylation in presence of high boiling solvent and alkali metal hydroxide as a catalyst in inert atmosphere, at high temperature to yield 2,6-diisopropylphenol (Propofol). Formation of major contaminants of Propofol i.e. ether impurity 1,3-di(propan-2-yl)-2-(propan-2-yloxy)benzene of Formula VII and monoalkylated phenol impurity 2-(propan-2-yl)phenol of Formula VIII are avoided.

The Propofol thus formed is further extracted using hydrocarbons solvents like toluene, xylene etc and then washing the organic layer with aqueous sodium bicarbonate and finally with water. The solvent is removed under reduced pressure and the residue is distilled off under high vacuum to give extra pure 2,6-disopropyl phenol free of the impurities described above.

Propofol prepared by the above method is highly pure and overcomes the drawbacks associated with impurity generation thus enabling its use in pharmaceutical compositions.

Accordingly in an aspect, the invention relates to pharmaceutical compositions comprising a therapeutically effective amount of highly pure 2,6-diisopropyl phenol (Propofol) of the present invention and a pharmaceutically acceptable excipients(s)/carrier(s). Further, the pharmaceutical composition of the invention may be a solid form, a liquid suspension or an injectable composition.

DESCRIPTION OF INVENTION

The invention will now be described in details in connection with certain preferred and optional embodiments so that various aspects thereof may be more fully understood and appreciated.

The present invention relates to a process for the preparation of highly pure 2,6-diisopropylphenol of formula I employing alkylation of p-hydroxy benzoic acid to form dialkylated p-hydroxy benzoic acid followed by decarboxylation.

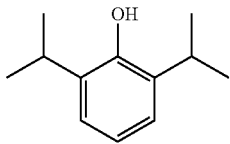

Formula I

In an embodiment, the process of the present invention comprises Friedel Craft's alkylation of p-hydroxybenzoic acid of Formula II in presence of acidic and/or dehydrating substance followed by basification with sodium hydroxide to produce 4-hydroxy-3,5-diisopropyl benzoic acid of Formula III.

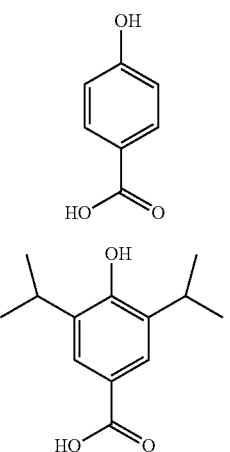

Formula II

Formula III

The alkylating agent can be selected from isopropyl alcohol, isopropyl halide, preferably isopropyl alcohol and the acidic and/or dehydrating substance is selected from aqueous mineral acid; preferably 85-95% w/w aqueous sulfuric acid. The reaction is carried out at the temperature in the range of 60-65° C.

Further, besides the desired product i.e. 4-hydroxy-3,5-diisopropyl benzoic acid of Formula III, other contaminants are also formed such as ether impurity 3,5-di(propan-2-yl)-4-(propan-2-yloxy)benzoic acid of Formula V(0.2-0.5%), dimer impurity, 4,4'-oxydibenzoic acid of Formula IV(2-10%) and the monoalkylated impurity 4-hydroxy-3-(propan-2-yl)benzoic acid of Formula VI (0.5-1.05%) which are removed by washings with solvent mixture.

The solvent that can be used for washings is selected from water, lower alcohols, hydrocarbons either alone or in combination thereof.

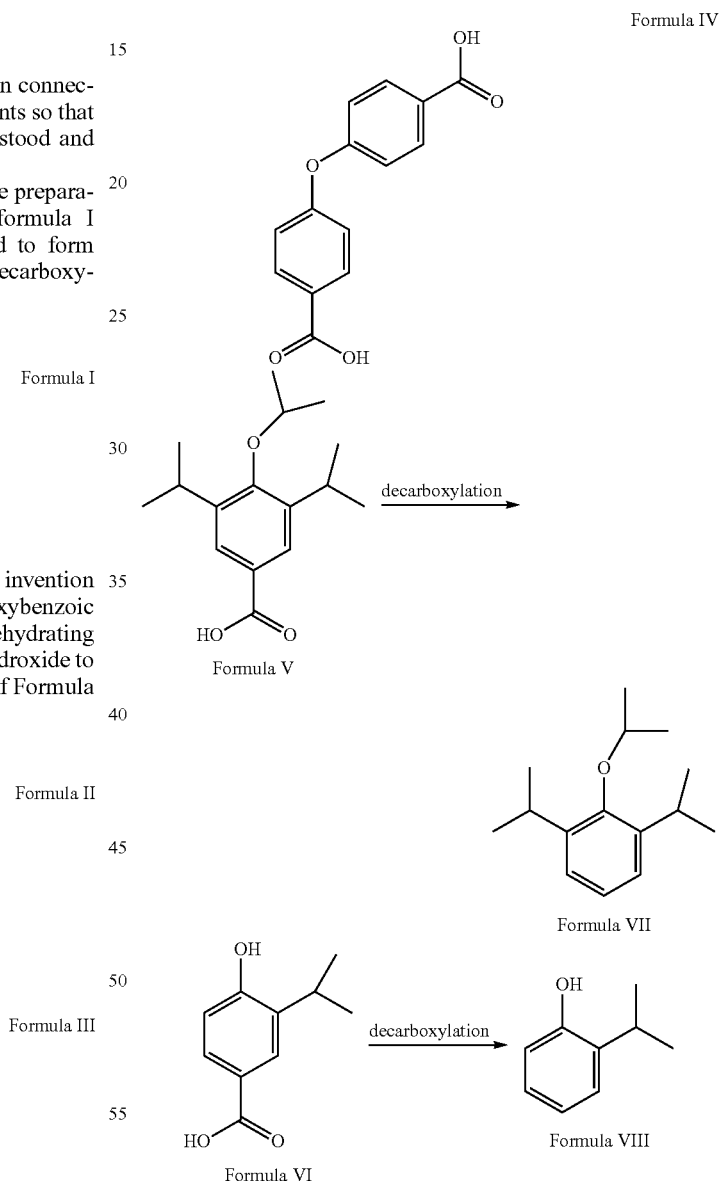

Accordingly, the ether impurity of Formula V is removed by washing of aqueous reaction mass at basic pH using toluene, while the dimer impurity of Formula IV is removed by repetitive hot water washing, whereas the monoalkylated impurity of Formula VI is removed by methanol-water purification. 4-hydroxy-3,5-diisopropyl benzoic acid of Formula III thus obtained is 99.85% pure. All the remaining impurities are below 0.05%. It is advantageous to carry out the purification of 4-hydroxy-3,5-diisopropyl benzoic acid of Formula III prior to decarboxylation stage as it inhibits impurities development at Propofol formation E.g. ether impurity 1,3-di(propan-2-yl)-2-(propan-2-yloxy)benzene of Formula VII and monoalkylated phenol impurity 2-(propan-2-yl)phenol of Formula VIII.

The alkylation of p-hydroxybenzoic acid rather than phenol itself in presence of acidic and/or dehydrating agent controls exhaustive alkylation and excessive formation of isomeric byproducts like 2,4 diisopropyl phenol and 2,4,6 triisopropyl phenols which are difficult to eliminate completely due to small differences in their boiling points. Further, p-hydroxybenzoic acid being an inexpensive commercially available reagent makes the invention more economic for manufacture of 2,6-diisopropylphenol.

In another embodiment, 4-hydroxy-3,5-diisopropyl benzoic acid of Formula III, substantially free from impurities mentioned above is subjected to decarboxylation in presence of high boiling solvent and alkali metal hydroxide as a catalyst in an inert atmosphere to yield 2,6-diisopropylphenol (Propofol). Formation of major contaminants of Propofol i.e. ether impurity 1,3-di(propan-2-yl)-2-(propan-2-yloxy)benzene of Formula VII and monoalkylated phenol impurity 2-(propan-2-yl)phenol of Formula VIII are avoided by using 4-hydroxy-3,5-diisopropyl benzoic acid substantially free from impurities of Formula III, IV and V. High boiling solvent facilitates to attain the desired temperature for decarboxylation. The inert environment in the reaction helps in reducing the impurity level at initial stage.

The Propofol thus formed is further extracted using hydrocarbon solvents like toluene, xylene etc and then washing the organic layer with aqueous sodium bicarbonate and finally with water. After removal of solvent, the residue is distilled off under high vacuum to give extra pure 2,6-diisopropyl phenol having purity of 99.90% and free from ether impurity 1,3-di(propan-2-yl)-2-(propan-2-yloxy)benzene of Formula VII and monoalkylated phenol impurity 2-(propan-2-yl)phenol of Formula VIII.

The catalyst used during decarboxylation is selected from alkali metal hydroxide such as sodium or potassium hydroxide. The temperature for the reaction is in the range of 120-160° C.

The high boiling point solvents used are preferably the solvents having boiling point above 130° C., and are selected from ethylene glycol, dimethylformamide or dimethylacetamide.

Propofol thus prepared by the above process is highly pure, overcomes the drawbacks associated with impurity generation and is suitable for pharmaceutical use.

Accordingly in an embodiment, the invention relates, to pharmaceutical compositions comprising a therapeutically effective amount of highly pure 2,6-diisopropyl phenol (Propofol) of the present invention and a pharmaceutically acceptable excipients(s)/carrier(s). Further, the pharmaceutical composition of the invention may be a solid form, a liquid suspension or an injectable composition. The active ingredient(s) and excipient(s)/carrier(s) can be formulated into compositions and dosage forms according to methods known in the art.

The 'therapeutically effective amount' as described above means and includes the amount required to treat/alleviate the severity of symptoms associated with this ailments as decided by the persons of ordinary skill in the art.

Further details of the process of the present invention will be apparent from the examples presented below. The examples presented are purely illustrative and are not limited to the particular embodiments illustrated herein but include the permutations, which are obvious as set forth in the description.

EXAMPLE 1

360 ml sulphuric acid was added slowly to 25 ml chilled water at 10-15° C. to a round bottom flask supplied with a mechanical stirrer. To this stirred mass was charged p-hydroxy benzoic acid 100 g (0.72M) lot wise followed by Isopropyl alcohol 130 g (2.16M) at a temperature below 15° C. The reaction mass was finally heated to 60-65° C. for 4 hrs. After reaction completion the reaction mass was quenched in caustic solution and washed two times with toluene (400 ml). The aqueous layer obtained was acidified using aq. HCl solution. Precipitated solid was washed twice, each time with 250 ml of hot water and dried to obtain crude product. Crude solid was dissolved in 350 ml of methanol and treated with activated carbon, filtered and added into 1000 ml chilled water at about 10-15° C. The precipitate was filtered off and washed twice with 200 ml of water each time. After drying under vacuum at 70-75° C. up to a constant weight, 4-hydroxy-3,5-diisopropyl benzoic acid was obtained.

120 g (74.6%) yield,
M.P. 147° C.,
Purity by HPLC 99.85%.

EXAMPLE 2

To the solution of 4-hydroxy-3,5-diisopropyl benzoic acid 100 g (0.45 M) (example 1) in ethylene glycol (150 ml) was added sodium hydroxide pallets 41.5 g (1.03M) and heated to 140-145° C. under inert atmosphere. After 7 hrs of continued heating at 140-145° C., the reaction mass was cooled to room temperature and diluted with 5 times water. The pH of the mass was then adjusted to 1-2 using concentrated Hydrochloric acid, reaction mixture was stirred for one hour and extracted three times with 200 ml toluene, combined toluene layers were washed twice with 5% aq. sodium bicarbonate solution (50 ml) and finally with water (200 ml), solvent was removed under reduced pressure and a dark brown colored residue which remained was distilled under high vacuum condition (0.2 mm/Hg) to yield 75 g (93.5%) of 2,6-diisopropyl phenol collected as a colourless to pale yellow oily liquid, HPLC Purity 99.93%.

The process as substantially described hereinabove is summarized below:

The process for the preparation of highly pure 2,6-diisopropyl phenol (Formula I), comprises reacting p-hydroxy benzoic acid (Formula II) with an alkylating agent in presence of aq. mineral acid at a temperature in the range of 60-65° C. followed by basification with sodium hydroxide to yield crude 4-hydroxy-3,5-diisopropylbenzoic acid (Formula III) including ether impurity 3,5-di(propan-2-yl)-4-(propan-2-yloxy)benzoic acid of Formula V, dimer impurity, 4,4'-oxydibenzoic acid of Formula IV, and the monoalkylated impurity 4-hydroxy-3-(propan-2-yl)benzoic acid of Formula VI and subsequently (a) washing with toluene at basic pH to remove the ether impurity 3,5-di(propan-2-yl)-4-(propan-2-yloxy)benzoic acid of Formula V; (b) washing with hot water to remove dimer impurity 4,4'-oxydibenzoic acid of Formula IV; (c) washing with methanol-water mixture, to remove monoalkylated impurity 4-hydroxy-3-(propan-2-yl)benzoic acid of Formula VI, followed by decarboxylation of 4-hydroxy-3,5-diisopropylbenzoic acid (Formula III), free from impurities of Formula IV, V and VI, in presence of high boiling solvent and a catalyst at high temperature to yield 2,6-diisopropyl phenol having purity of 99.9% by HPLC. 2,6-diisopropyl phenol thus obtained is substantially free of ether impurity 1,3-di(propan-2-yl)-2-(propan-2-yloxy)benzene of Formula VII and monoalkylated phenol impurity 2-(propan-2-yl) phenol of Formula VIII.

The invention further relates to pharmaceutical composition comprising a therapeutically effective amount of highly pure 2,6-diisopropyl phenol (Propofol) prepared by process as claimed in claim 1 along with pharmaceutically acceptable excipients(s)/carrier(s).

We claim:

1. A process for the preparation of highly pure 2,6-diisopropyl phenol of Formula I,

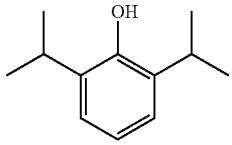

Formula I said process comprising:
(a) reacting p-hydroxy benzoic acid of Formula II with an alkylating agent in the presence of an aqueous mineral acid at a temperature of between 60° C. and 65° C. to produce crude 4-hydroxy-3,5-diisopropylbenzoic acid of Formula III, said crude 4-hydroxy-3,5-diisopropylbenzoic acid comprising at least one impurity selected from the group consisting of:

3,5-di(propan-2-yl)-4-(propan-2-yloxy)benzoic acid of Formula V;

4,4'-oxydibenzoic acid of Formula IV; and 4-hydroxy-3-(propan-2-yl)benzoic acid of Formula VI;

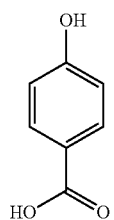

Formula II

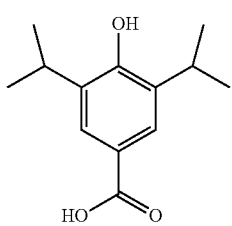

Formula III

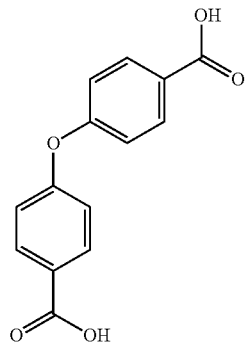

Formula IV

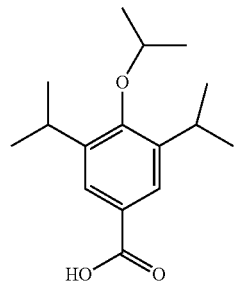

Formula V

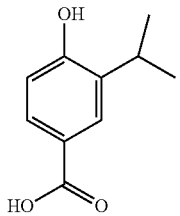

Formula VI (b) removing said at least one impurity from said crude 4-hydroxy-3,5-diisopropylbenzoic acid by performing at least one step selected from the group consisting of:
  i) washing said crude 4-hydroxy-3,5-diisopropylbenzoic acid with toluene at a basic pH to remove 3,5-di(propan-2-yl)-4-(propan-2-yloxy)benzoic acid of Formula V;
  ii) washing said crude 4-hydroxy-3,5-diisopropylbenzoic acid with hot water to remove 4,4'-oxydibenzoic acid of Formula IV; and
  iii) removing 4-hydroxy-3-(propan-2-yl)benzoic acid of Formula VI from said crude 4-hydroxy-3,5-diisopropylbenzoic acid by either:
    washing said crude 4-hydroxy-3,5-diisopropylbenzoic acid with a mixture of methanol and water, or
    recrystallizing said crude 4-hydroxy-3,5-diisopropylbenzoic acid from a mixture of methanol and water; and
(c) decarboxylating the 4-hydroxy-3,5-diisopropylbenzoic acid produced in step (b) in the presence of a high boiling solvent and a catalyst at high temperature to yield 2,6-diisopropyl phenol.

2. The process of claim 1, wherein step (b) comprises performing at least two steps selected from the group consisting of:
  i) washing said crude 4-hydroxy-3,5-diisopropylbenzoic acid with toluene at a basic pH to remove 3,5-di(propan-2-yl)-4-(propan-2-yloxy)benzoic acid;
  ii) washing said crude 4-hydroxy-3,5-diisopropylbenzoic acid with hot water to remove 4,4'-oxydibenzoic acid; and iii) removing 4-hydroxy-3-(propan-2-yl)benzoic acid from said crude 4-hydroxy-3,5-diisopropylbenzoic acid by either:
  washing said crude 4-hydroxy-3,5-diisopropylbenzoic acid with a mixture of methanol and water, or
  recrystallizing said crude 4-hydroxy-3,5-diisopropylbenzoic acid from a mixture of methanol and water.

3. The process of claim 1, wherein step (b) comprises sequentially:
  i) washing said crude 4-hydroxy-3,5-diisopropylbenzoic acid with toluene at a basic pH to remove 3,5-di(propan-2-yl)-4-(propan-2-yloxy)benzoic acid;
  ii) washing said crude 4-hydroxy-3,5-diisopropylbenzoic acid with hot water to remove 4,4'-oxydibenzoic acid; and
  iii) removing 4-hydroxy-3-(propan-2-yl)benzoic acid from said crude 4-hydroxy-3,5-diisopropylbenzoic acid by recrystallizing said crude 4-hydroxy-3,5-diisopropylbenzoic acid from a mixture of methanol and water.

4. A process for the preparation of highly pure 4-hydroxy-3,5-diisopropylbenzoic acid, said process comprising:
  (a) reacting p-hydroxy benzoic acid with an alkylating agent in the presence of an aqueous mineral acid at a temperature of between 60° C. and 65° C. to produce a reaction mixture comprising crude 4-hydroxy-3,5-diisopropylbenzoic acid, said reaction mixture further comprising at least one impurity;
  (b) recovering said crude 4-hydroxy-3,5-diisopropylbenzoic acid;
  (c) removing said at least one impurity by performing at least one step selected from the group consisting of:
    i) washing said reaction mixture with toluene at a basic pH prior to step (b);
    ii) washing the crude 4-hydroxy-3,5-diisopropylbenzoic acid obtained in step (b) with hot water; and
    iii) either washing the crude 4-hydroxy-3,5-diisopropylbenzoic acid obtained in step (b) with a mixture of methanol and water; or recrystallizing the crude 4-hydroxy-3,5-diisopropylbenzoic acid obtained in step (b) from a mixture of methanol and water.

5. The process of claim 4, wherein said at least one impurity is selected from the group consisting of 3,5-di(propan-2-yl)-4-(propan-2-yloxy)benzoic acid; 4,4'-oxydibenzoic acid; and 4-hydroxy-3-(propan-2-yl)benzoic acid.

6. The process of claim 5, wherein:
  said step of washing said reaction mixture with toluene removes 3,5-di(propan-2-yl)-4-(propan-2-yloxy)benzoic acid from said reaction mixture;
  said step of washing the crude 4-hydroxy-3,5-diisopropylbenzoic acid with hot water removes 4,4'-oxydibenzoic acid; and
  said step of either washing the crude 4-hydroxy-3,5-diisopropylbenzoic acid with a mixture of methanol and water; or recrystallizing the crude 4-hydroxy-3,5-diisopropylbenzoic acid removes 4-hydroxy-3-(propan-2-yl)benzoic acid.

7. The process as claimed in claim 1, wherein step (a) comprises reacting p-hydroxy benzoic acid with an alkylating agent in the presence of an aqueous mineral acid at a temperature of between 60° C. and 65° C., wherein said aqueous mineral acid 85-95% w/w aqueous sulfuric acid.

8. The process as claimed in claim 1, wherein the high boiling solvent of step (c) is selected from the group consisting of ethylene glycol, dimethylformamide and dimethylacetamide.

9. The process as claimed in claim 1, wherein the catalyst of step (c) is an alkali metal hydroxide.

10. The process as claimed in claim 1, wherein the 2,6-diisopropylphenol produced in step (c) is at least 99.9% pure by HPLC.

11. The process as claimed in claim 2, wherein the 2,6-diisopropylphenol produced in step (c) is at least 99.9% pure by HPLC.

12. The process as claimed in claim 3, wherein the 2,6-diisopropylphenol produced in step (c) is at least 99.9% pure by HPLC.

13. A process for the preparation of a pharmaceutical composition comprising highly pure 2,6-diisopropyl phenol, said process comprising:
  (a) reacting p-hydroxy benzoic acid with an alkylating agent in the presence of an aqueous mineral acid at a temperature of between 60° C. and 65° C. to produce a reaction mixture comprising crude 4-hydroxy-3,5-diisopropylbenzoic acid, said reaction mixture further comprising at least one impurity;
  (b) recovering said crude 4-hydroxy-3,5-diisopropylbenzoic acid;
  (c) removing said at least one impurity by performing at least one step selected from the group consisting of:
    i) washing said reaction mixture with toluene at a basic pH prior to step (b);
    ii) washing the crude 4-hydroxy-3,5-diisopropylbenzoic acid obtained in step (b) with hot water; and
    iii) either washing the crude 4-hydroxy-3,5-diisopropylbenzoic acid obtained in step (b) with a mixture of methanol and water; or recrystallizing the crude 4-hydroxy-3,5-diisopropylbenzoic acid obtained in step (b) from a mixture of methanol and water;
  (d) decarboxylating the 4-hydroxy-3,5-diisopropylbenzoic acid produced in step (b) in the presence of a high boiling solvent and a catalyst at high temperature to yield 2,6-diisopropyl phenol; and
  (e) combining said 2,6-diisopropyl phenol with at least one pharmaceutically acceptable excipient or vehicle to produce said pharmaceutical composition.

14. A method of making 2,6-diisopropyl phenol, comprising:
  a step of decarboxylating 4-hydroxy-3,5-diisopropylbenzoic acid produced by the process of claim 4 in the presence of a high boiling solvent and a catalyst at high temperature.

15. The process of claim 14, wherein step (c) comprises performing at least two steps selected from the group consisting of:
  i) washing said reaction mixture with toluene at a basic pH prior to step (b);
  ii) washing the crude 4-hydroxy-3,5-diisopropylbenzoic acid obtained in step (b) with hot water; and
  iii) either washing the crude 4-hydroxy-3,5-diisopropylbenzoic acid obtained in step (b) with a mixture of methanol and water; or recrystallizing the crude 4-hydroxy-3,5-diisopropylbenzoic acid obtained in step (b) from a mixture of methanol and water.

16. The process of claim 15, wherein step (c) comprises:
  i) washing said reaction mixture with toluene at a basic pH prior to step (b);
  ii) washing the crude 4-hydroxy-3,5-diisopropylbenzoic acid obtained in step (b) with hot water; and
  iii) recrystallizing the crude 4-hydroxy-3,5-diisopropylbenzoic acid obtained in step (b) from a mixture of methanol and water.

* * * * *